United States Patent [19]
Ekwall

[11] Patent Number: 5,601,614
[45] Date of Patent: Feb. 11, 1997

[54] METHOD AND DEVICE FOR DETERMINING WHETHER ELECTRICAL SIGNALS IN A HEART ARE CAUSED BY AN ATRIAL DEPOLARIZATION

[75] Inventor: Christer Ekwall, Spanga, Sweden

[73] Assignee: Pacesetter AB, Solna, Sweden

[21] Appl. No.: 227,325

[22] Filed: Apr. 14, 1994

[30] Foreign Application Priority Data

May 12, 1993 [SE] Sweden .................................. 9301628

[51] Int. Cl.$^6$ .................................................. A61N 1/362
[52] U.S. Cl. ................................................................ 607/25
[58] Field of Search ............................. 607/122, 25, 9; 128/696, 703, 704, 702

[56] References Cited

U.S. PATENT DOCUMENTS

| | | |
|---|---|---|
| 4,343,311 | 8/1982 | Markowitz . |
| 4,444,195 | 4/1984 | Gold . |
| 4,712,554 | 12/1987 | Garson, Jr. . |
| 4,905,696 | 3/1990 | Amundson et al. . |
| 5,156,149 | 10/1992 | Hudrik . |
| 5,174,289 | 12/1992 | Cohen . |
| 5,265,601 | 11/1993 | Mehra ......................................... 607/9 |
| 5,312,445 | 5/1994 | Nappholz et al. ........................... 607/9 |

OTHER PUBLICATIONS

"Cineventriculographic Analysis of the Ventricular Septal Motion during Stimulation of Various Pacemaker Sites," Miyazawa et al. Tohoku J. Exp. Med., vol. 126, No. 4, Dec., 1978, pp. 363–369.

Primary Examiner—William E. Kamm
Assistant Examiner—Scott M. Getzow
Attorney, Agent, or Firm—Hill, Steadman & Simpson

[57] ABSTRACT

In a method and apparatus for determining whether electrical signals in a heart are caused by atrial depolarizations or ventricular depolarizations, heart signals are sensed in the upper part of the ventricular heart tissue, preferably the upper part of the ventricular septum. The detection of heart signals from both the atrium and ventricle and the identification of depolarization is facilitated if the course of the signals is monitored, with monophasic heart signals being caused by an atrial depolarization and biphasic signals being caused by a ventricular depolarization.

16 Claims, 4 Drawing Sheets

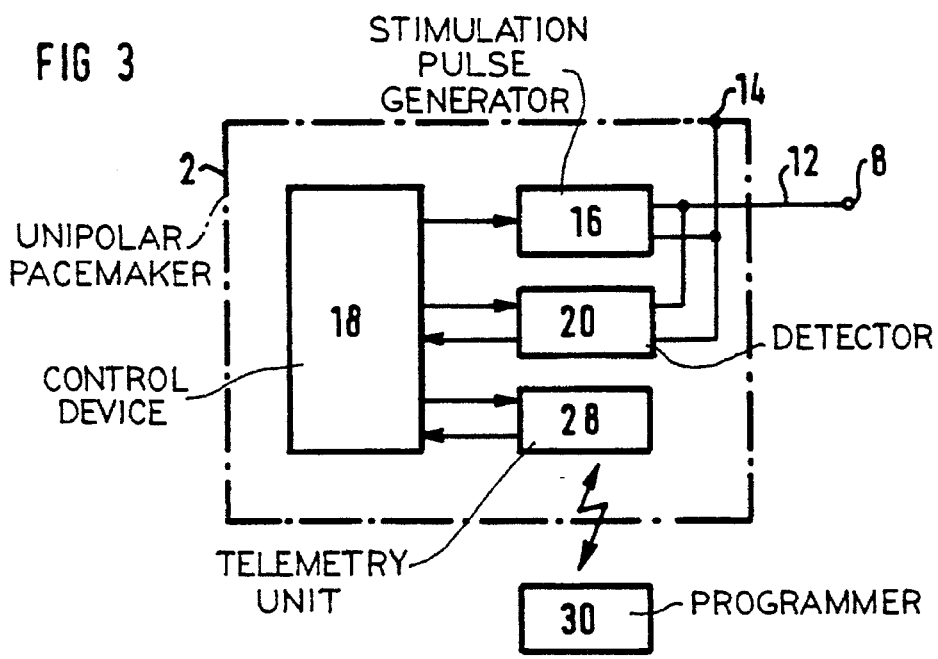
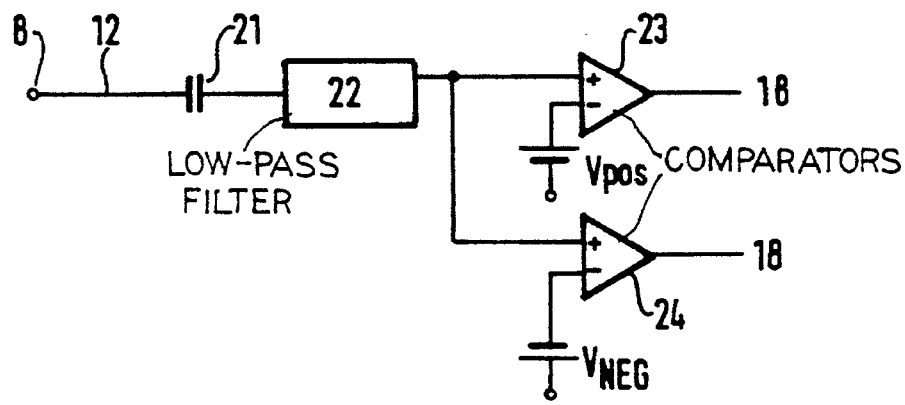
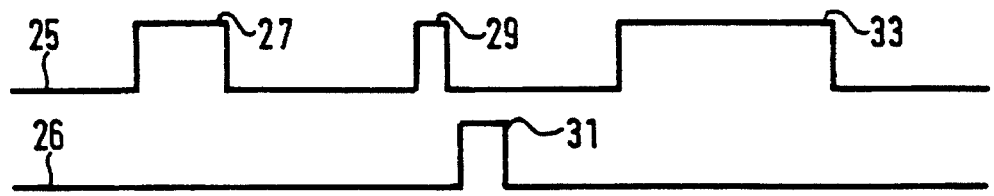

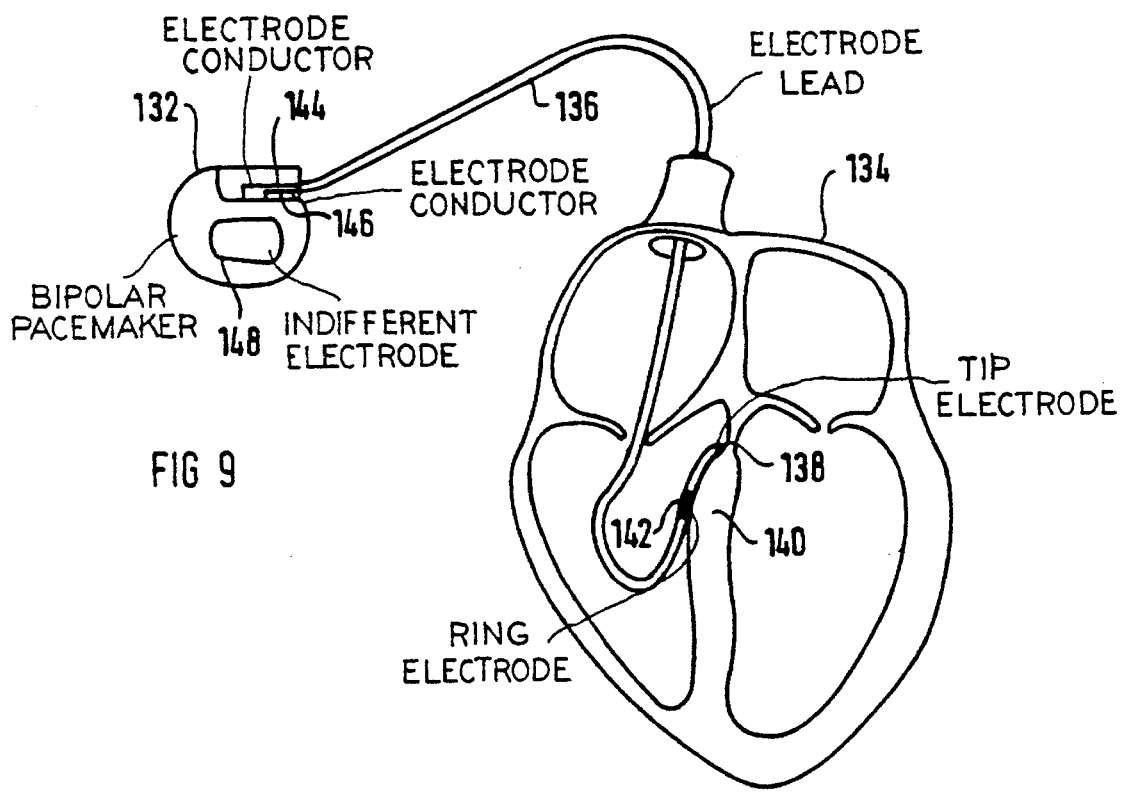
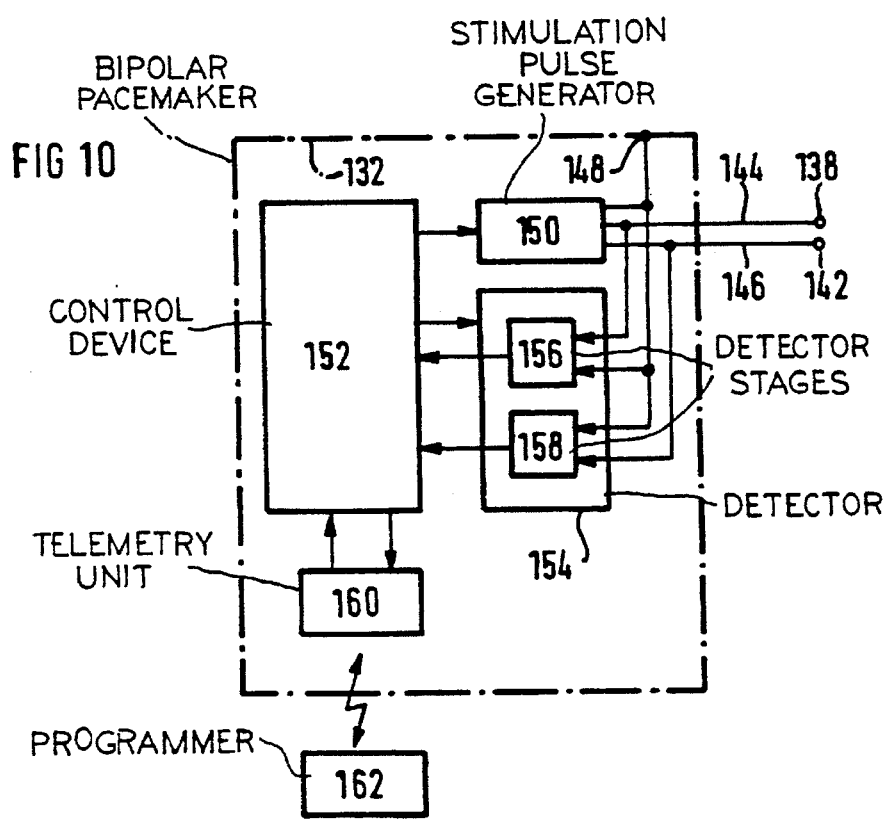

METHOD AND DEVICE FOR DETERMINING WHETHER ELECTRICAL SIGNALS IN A HEART ARE CAUSED BY AN ATRIAL DEPOLARIZATION

BACKGROUND OF THE INVENTION

1. Field of the Invention

The present invention is directed to a method and apparatus for determining whether electrical signals in a heart are caused by an atrial depolarization or a ventricular depolarization of the type wherein electrical signals are sensed with an electrode surface in contact with ventricular heart tissue and the sensed electrical signals are analyzed to distinguish whether they were caused by atrial depolarizations or were caused by ventricular depolarizations.

2. Description of the Prior Art

In a healthy heart, a heartbeat commences with a spontaneously generated electrical impulse in the sinus node. The impulse first induces atrial depolarization resulting in contraction of atrial heart muscle (atrial systole). The contraction of atrial musculature pumps blood from the respective atrium down to the ventricles. After a delay, the impulse is then conducted to the ventricles via the A-V node and causes ventricular depolarization, resulting in a contraction of ventricular heart muscle (ventricular systole). The contraction of ventricular muscle expels blood out of the heart into the systemic circulation and the pulmonary circulation. Heart tissue in the atrium and ventricle then repolarizes, and the muscle tissue relaxes (diastole). The heart then refills with blood from the veins. As the sinus node generates a new impulse, the cycle restarts.

For people with certain heart defects, a pacemaker can be an excellent aid which is capable of taking over stimulation of heart tissue when natural, spontaneous self-stimulation is inoperative. When e.g., the A-V node blocks transmission of signals from the atria but the sinus node works properly so as to trigger atrial depolarization in a natural way, a pacemaker capable of stimulating ventricular heart tissue, so the stimulated heart cycle resembles a healthy heart's cardiac cycle as closely as possible, is advantageous.

In order to achieve such pacing, it must be possible to detect atrial depolarizations at the same time as it must be possible to deliver stimulation pulses to the ventricular tissue. For this purpose, the use of dual chamber pacemakers, in which a first electrode with an electrode surface is placed in the right atrium to sense atrial depolarizations and a second electrode with an electrode surface is placed in the apex of the right ventricle to stimulate the ventricular tissue, is known. One such pacemaker is described in U.S. Pat. No. 4,343,311. At least two electrodes must be introduced into the heart, making the system more complex. Complications can develop during the implantation of the electrodes, and there is an increased risk of faults. In addition, a plurality of electrodes impedes the return of blood to the heart to some extent.

In order to reduce the number of electrodes which must be introduced into the heart via the venous system, a multipolar electrode can be employed having at least one electrode surface in the ventricle to stimulate same and at least one electrode surface in the atrium to sense atrial depolarizations, one such electrode is described in U.S. Pat. No. 4,444,195. For reliable detection of atrial depolarizations, the electrode surface in the atrium should be in close proximity to atrial tissue. The electrode must therefore be so stiff that it remains in virtually constant contact with atrial tissue. This could irritate heart tissue during the muscular contractions. Also, in general, a multipolar electrode also has a larger diameter than a unipolar electrode.

Both when a plurality of electrodes, each with one electrode conductor, is used and when multipolar electrodes, with a plurality of electrode conductors, is used, conductor breakage is always a risk. The more conductors employed, the greater the likelihood that one of them has a slight defect or reduced abrasion resistance, despite careful fabrication and quality control.

In U.S. Pat. No. 4,905,696 a detector is described which unipolarly measures heart impedance in the ventricle, and from the impedance signal atrial depolarizations can be identified as fast, brief changes.

In a Swedish patent application No 9203642-5, corresponding co-pending U.S. application Ser. No. 08/152,126 filed Nov. 16, 1993 entitled "Detector for Sensing Events in Living Tissue" (Sivard et al.) and assigned to the assignee of the subject matter claimed herein, a detector is described which has at least two integrators. The heart's electrical signals are sensed. Monophasic and biphasic signals can be distinguished by the respective integrators integrating signals with different polarity. Since depolarizations in the atrium are monophasic when the signal is sensed in the ventricle and ventricular depolarizations are biphasic when sensed in the ventricle, this detector can distinguish between depolarization in the atrium and ventricle respectively on the basis of electrical signals detected unipolarly in the ventricle. The aforementioned patent application, however, like the other prior art described, does not consider the way the signals should be picked-up so that the most reliable discrimination which is possible is achieved. This co-pending application, nor the prior art, moreover do not address the problem of how to reduce the irritation to which heart tissue is subjected due to employed electrodes.

SUMMARY OF THE INVENTION

An object of the invention is to provide a method for distinguishing atrial depolarizations from ventricular depolarizations, when electrical signals are sensed in the ventricle, in the safest and most effective way possible. The method should simultaneously permit the most natural possible stimulation of the ventricle, and the electrode implanted in the heart will impede heart movements as little as possible.

A further object of the invention is to provide an apparatus constructed and operating in accordance with the inventive method.

The above object is achieved in accordance with the invention in a method and apparatus wherein the electrode surface used for sensing is positioned in the heart so that it senses the electrical signals in the part of the ventricular tissue located nearest the atrial half of the heart.

Sensing of electrical signals in the upper part of the ventricle's heart tissue makes it easier to detect signals from both the atrium and ventricle. Different types of detectors can be used for discriminating signals. A few are described in conjunction with the description of a device for performing the method. To sense electrical signals in the upper part of the ventricle, the electrode is introduced into the heart in such a way that it assumes a gradual bend in the ventricle, for example a bend having a diameter of approximately 2 cm, and the electrode surface is positioned so it becomes embedded in heart tissue. The electrode's gradual bend will reduce the irritation caused by the electrode conductor during the heart's contraction phase. This is because the heart pulls the septum between the atrium and ventricle (the valve plane), at which outlets into the blood circulations are located, downwardly toward the apex during each ventricular contraction. The gradual bend resiliently distributes the electrode's surface over a larger part of the heart tissue. Mechanical pressure exerted by the electrode during contraction movements is therefore reduced. The risk of inflammation, etc. in tissue accordingly declines. The mechanical load on the electrode and the risk of fatigue failure also decline simultaneously.

It is advantageous if the first electrode is positioned so it senses electrical signals in the ventricular septum.

Since the depolarization wave in a healthy heart is conducted to the ventricle via the A-V node, which is situated in the upper part of the ventricular septum, this electrode position will simplify the sensing and identification of atrial signals, since the electrode surface will be closer to atrial musculature. Moreover, this position will produce the most natural depolarization effect possible when the ventricle is stimulated. As previously noted, atrial depolarizations are experienced as being monophasic when sensed in the ventricle, and ventricular depolarizations are experienced as biphasic. It is therefore an advantage if atrial depolarizations are distinguished from ventricular depolarizations by determining whether the sensed electrical signals have a monophasic or biphasic course (signal curve), whereby monophasic courses are interpreted as atrial depolarizations and biphasic courses are interpreted as ventricular depolarizations. In addition, the biphasic aspect of the signal for the ventricular depolarization will be more pronounced when measurement occurs high up in the ventricle, compared to measurement in the apex. A detector capable of doing this is, as noted above, the subject of a co-pending patent application. Other detectors will be described below.

To increase reliability in the identification of atrial depolarization, it is advantageous if the duration of the monophasic courses is determined, and only monophasic courses with a duration less than a predetermined duration are interpreted as atrial depolarizations. This means that even though ventricular repolarizations, which also have a monophasic course, are sensed, these can easily be distinguished from the atrial depolarizations, since the former has a much longer duration.

In a refinement of the method is achieved in accordance with the invention, a second electrode surface senses electrical signals on or near the ventricular septum at a predetermined distance from the first (aforementioned) electrode surface toward the apex, and the chronological sequence in which electrical signals are sensed by the two electrode surfaces is determined. Electrical signals which are sensed by the second electrode surface before being sensed by the first electrode surface are interpreted as ventricular depolarizations.

In the upper part of the ventricular septum, i.e. about the upper third, ventricular depolarization has a propagation direction from the bottom upwardly toward the septum between the ventricle and atrium. A sensed atrial depolarization, however, is propagated in the opposite direction. By determining threshold values for the signals to be sensed by the first and second electrode surface respectively, a detection criterion can be obtained in which atrial depolarization is only sensed by the first electrode surface, whereas ventricular depolarization and repolarization are sensed by both the first and the second electrode surfaces.

A device for determining whether electrical signals in a heart are caused by an atrial depolarization or a ventricular depolarization, has an electrode lead with a first electrode surface, a detector for sensing electrical signals via the first electrode surface and a control device for distinguishing atrial depolarizations from ventricular depolarizations on the basis of the electrical signals sensed by the detector, with the electrode lead being designed to be introduced into the right ventricle and positioned with a gentle bend so the first electrode surface is attachable to the upper part of the ventricular septum, and the detector includes means for distinguishing between signals caused by atrial depolarizations and signals caused by ventricular depolarizations.

A unipolar device is achieved in accordance with the invention wherein the means for distinguishing between signals caused by atrial depolarizations and signals caused by ventricular depolarizations is formed by a low-pass filter for eliminating high-frequency noise, a first comparator, which compares the amplitude of the filtered signal with a first threshold value and emits an output signal when the filtered signal's amplitude exceeds the first threshold value, and a second comparator, which compares the amplitude of the filtered signal with a second threshold value and emits an output signal when the filtered signal's amplitude is less than the second threshold value. The control device interprets signals which result in the generation of an output signal only from the first comparator as an atrial depolarization and signals generating an output signal from both comparators are interpreted as a ventricular depolarization.

Since the signals can be discriminated because atrial depolarizations are monophasic, whereas ventricular depolarizations are biphasic, identification of the respective signal with a detector, in which the signal's amplitude is compared with a threshold value on either side of a baseline level, is simple. Monophasic signals can only satisfy the condition for one threshold value, whereas a biphasic signal can satisfy conditions for both threshold values.

In this context, it is advantageous if the control device includes a timer for measuring the time during which the first comparator emits an output signal, whereby sensed heart signals which generate an output signal from the first comparator with a duration less than a predetermined duration are interpreted as arising due to an atrial depolarization. This prevents spurious interpretation of ventricular repolarization as atrial depolarization.

One alternative embodiment of a unipolar device is achieved in accordance with the invention wherein the means for distinguishing between signals caused by atrial depolarizations and signals caused by ventricular depolarizations includes an integrator, which integrates the sensed signals, and a comparator, which compares the integrated signals with a predetermined threshold value and generates an output signal when the amplitude of the integrated signals exceeds the predetermined threshold value, and wherein the control device includes a timer which measures the time during which the amplitude of the integrated signals exceeds the predetermined threshold value. The control device interprets a duration less than a first predetermined value as representative of a ventricular depolarization and a duration greater than the first predetermined value as representative of an atrial depolarization.

Since the biphasic signal has both positive and negative signal components, this signal will exceed the threshold value during integration only for a short period of time, whereas the integral of the monophasic signal will exceed the threshold value for a longer period of time.

In this context, it is advantageous if the control device also compares the duration with a second predetermined value, which is greater than the first predetermined value, whereby a duration greater than the first predetermined value but less than the second predetermined value is interpreted as an atrial depolarization.

In this manner, atrial depolarization can, in this embodiment, also be distinguished from ventricular repolarization when these are present in the signals to the detector.

A third unipolar device is achieved in accordance with the invention wherein the means for distinguishing between signals caused by atrial depolarizations and signals caused by ventricular depolarizations includes a first integrator, which integrates signal components with positive polarity, and a second integrator, which integrates signal components with negative polarity, and wherein the control device interprets monophasic signals as atrial depolarizations and biphasic signals as ventricular depolarizations.

A bipolar device is achieved in accordance with the invention wherein the electrode lead carries a second electrode surface by means of which the detector can sense electrical signals from the ventricular tissue, the second electrode surface being located at a predetermined distance from the first electrode surface. The second electrode surface is in contact with the ventricular septum in a position located at the predetermined distance from the first electrode surface toward the apex. The means for distinguishing between signals caused by atrial depolarizations and signals caused by ventricular depolarizations includes a first detector stage connected to the first electrode surface and to the control device and a second detector stage connected to the second electrode surface and to the control device, and the control device interprets electrical signals detected by the second electrode surface before being detected by the first electrode surface as ventricular depolarizations.

For both the unipolar and bipolar versions, it is advantageous if the apparatus further includes a pulse generator for generating and emitting stimulation pulses to the ventricular tissue via the first electrode surface, and the control device controls the pulse generator on the basis of the electrical signals sensed by the detector and on the aforementioned interpretation thereof.

DESCRIPTION OF THE DRAWINGS

FIG. 3 is a block diagram showing the structure of the unipolar pacemaker of FIG. 1 in greater detail.

FIG. 4 illustrates a first embodiment of a detector which can separate monophasic signals from biphasic signals for use in the apparatus of the invention.

FIG. 5 illustrates the output signals from the detector of FIG. 4 according to the first embodiment.

FIG. 9 shows an embodiment of a bipolar pacemaker constructed and operating in accordance with the principles of the present invention.

FIG. 10 is a block diagram showing the structure of the bipolar pacemaker of FIG. 9 in greater detail.

DESCRIPTION OF THE PREFERRED EMBODIMENTS

Figure 1:
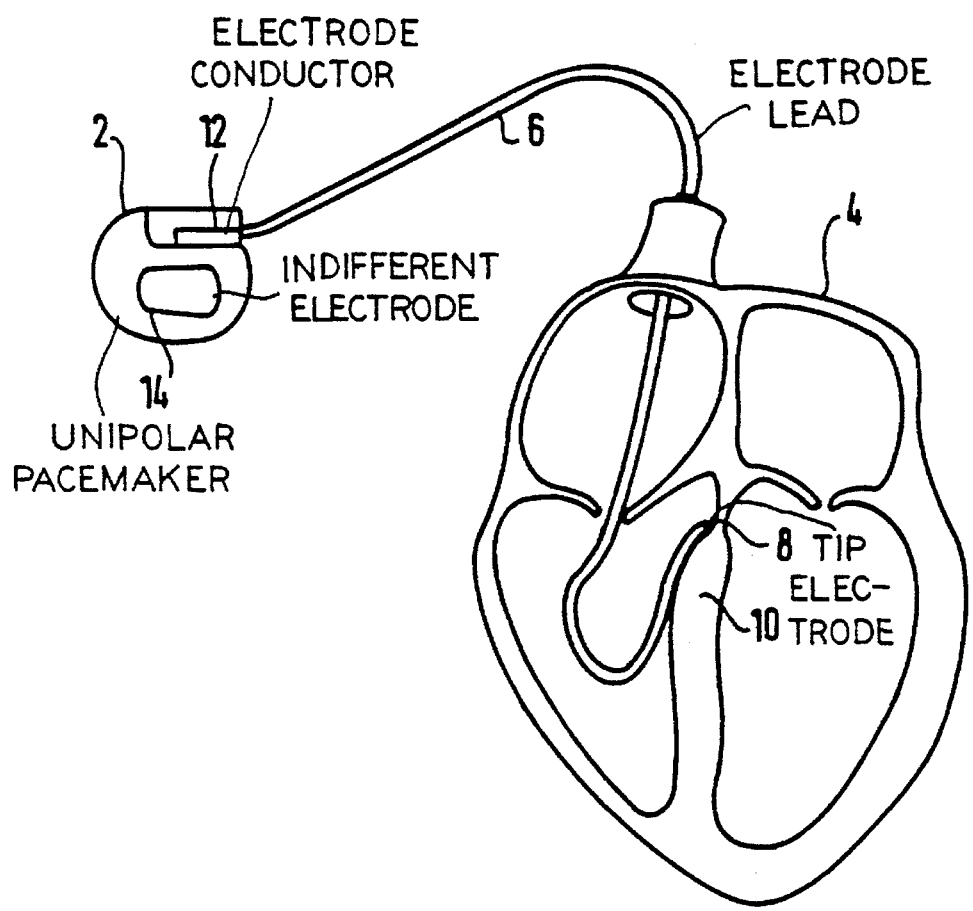
FIG. 1 shows an embodiment of a unipolar pacemaker constructed and operating in accordance with the principles of the present invention.

A unipolar pacemaker 2, as shown in FIG. 1, is connected to a heart 4 by an electrode lead 6. A tip electrode 8 is disposed at the end of the electrode lead 6. The tip electrode 8 is attached to the upper part of the ventricular septum 10 in the right ventricle of the heart 4. The electrode lead 6 has an electrode conductor 12, which connects the tip electrode 8 to pacemaker electronics. An indifferent electrode 14 is disposed on the pacemaker 2, which is placed so a stimulation pulse can be delivered to the heart 4 from the pacemaker 2 via the electrode lead 6 and the tip electrode 8 to the septum 10. The stimulation pulse is then conducted back through body tissue to the indifferent electrode 14. The electrical signals of the heart can also be sensed via the tip electrode 8.

The gradual bend in the electrode lead 6 in the ventricle and the position of the tip electrode 8 high up in the septum 10 cause less irritation to heart tissue than if the tip electrode 8 were located in the apex. Since the heart muscle's contraction pulls the valve plane down towards the apex in order to pump blood out into the respective blood circulation routes, the surface of the electrode lead 6 is distributed over a larger part of heart tissue, and the lead resiliently follows changes in the shape of the ventricle. The gradual bend and the position high up in the septum 10 do not impede the heart Is natural movements, and the load on the electrode conductor 12 is also reduced.

Figure 2:
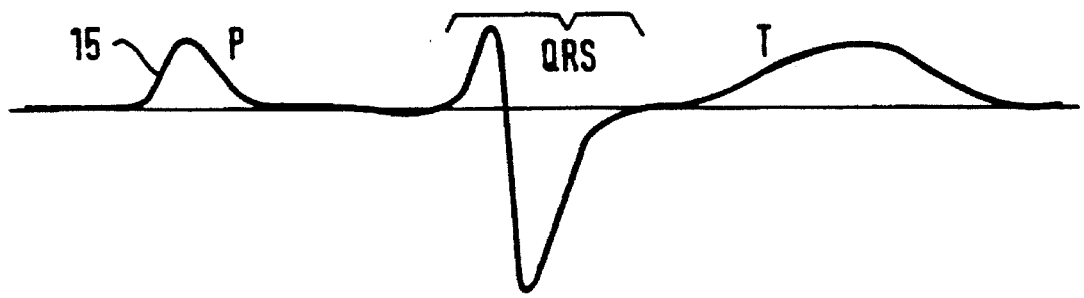
FIG. 2 illustrates the electrical signal picked up from a heart in accordance with the invention.

Heart signals 15 are sensed through the tip electrode 8, as shown in FIG. 2. Heart signals can be divided into three groups; the atrial depolarization, i.e., the P-wave, followed by the ventricular depolarization, i.e., the QRS-wave, and the ventricular repolarization, i.e., the T-wave. The atrium is also repolarized, but the signal from this repolarization is generally "swamped" by the QRS wave. As the signal 15 shows, the P-wave and the T-wave are monophasic, whereas the QRS wave is biphasic. This is utilized in the unipolar pacemaker 2 to reliably distinguish between atrial depolarization and ventricular depolarization.

The unipolar pacemaker 2 in FIG. 3 is shown in a block diagram. A pulse generator 16 generates stimulation pulses and deliver same, via the electrode conductor 12, to the tip electrode 8. The pulse generator 16 is also connected to the indifferent electrode 14. The emission of stimulation pulses by the pulse generator 16 and the amplitude and duration of the stimulation pulses are controlled by a control device 18. A detector 20 is connected in parallel across the output terminal of the pulse generator 16 in order to sense heart signals. The position of the electrode tip 8 high up on the septum 10 (FIG. 1) simplifies detection by the detector 20 of signals from both the atrium and the ventricle. The sensing of heart signals by the detector 20 and determination of the threshold level for detectable signals are controlled by the control device 18.

The pacemaker 2 also includes a telemetry unit 28 which is connected to the control device 18. Via the telemetry unit 28, information can be transmitted to/from the control device 18 from/to an extracorporeal programming unit 30.

A first embodiment of the detector 20 is shown in FIG. 4. The tip electrode 8 is connected by the electrode conductor 12 to a capacitor 21 which eliminates DC components and maintains a given baseline level for the signal. The sensed signals are then fed through a low-pass filter 22, preferably with a limit frequency of 100 Hz, to reduce noise from muscle signals and other noise. The filtered signal then goes to a first comparator 23 and a second comparator 24. The filtered signal is compared with a positive threshold value $V_{POS}$ in the first comparator 23, and the filtered signal is compared with a negative threshold value $V_{NEG}$ in the second comparator. The two thresholds can have the same or different absolute values. The first comparator 23 and the second comparator 24 respectively generate an output signal as long as the filtered signal is greater than the first threshold value or is less than the second threshold value. Output signals from the comparators 23 and 24 are sent to the control device 18.

FIG. 5 illustrates the output signals from the respective comparator 23 and 24 the input signal 15 to the detector 20 as shown in FIG. 2. The signal 25 is the output signal from the first comparator 23, and the signal 26 is the output signal from the second comparator 24. The P-wave from the signal 15 in FIG. 2 will generate a square wave 27 from the first comparator 23, the QRS-wave will generate a brief square wave 29 from the first comparator 23 and a brief square wave 31 from the second comparator 24 and the T-wave will generate a long-duration square wave 33 from the first comparator 23. Since the second comparator 24 only generates an output signal when a biphasic signal is present, ventricular depolarizations are very easy to identify. Since the T-wave generates a long square wave 33, the control device 18 can appropriately be devised so that only output signals from the first comparator 23 which are less than a predetermined duration are interpreted as atrial depolarization.

Figure 6:
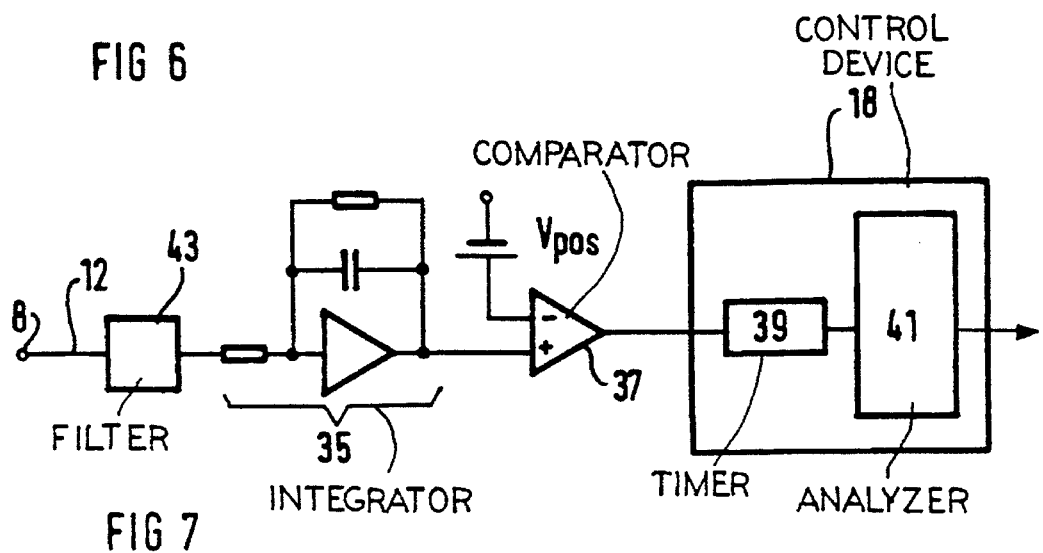
FIG. 6 shows a second embodiment of a detector which can separate monophasic from biphasic signals for use in the apparatus of the invention.

In FIG. 6 is shown a second embodiment of the detector 20 which can distinguish between monophasic and biphasic signals. The signal sensed by the tip electrode 8 is sent via the electrode conductor 12 to a filter 43. The filter can be a low-pass type, like the filter 22 in FIG. 4, but could alternatively be a band-pass type if removal of the low-frequency T-wave is desired. The filtered signal is integrated in an integrator 35 and then compared in a comparator 37 with a threshold value $V_{POS}$. The integrator 35 has a DC roll-off to prevent saturation and to steer the signal down toward a baseline level. The DC roll-off is selected so the integrated signal after an atrial depolarization returns to the baseline level before the QRS wave arrives. The resistances and capacitance of the integrator 35 can be selected so that the DC roll-off amounts to about 15 Hz.

The output signal from the comparator 37 is sent to the control device 18 which first determines, with a timer 39, the duration of the output signals from the comparator 37. Measured durations are sent to an analyzer 41 which establishes the type of signal detected.

Figure 7:
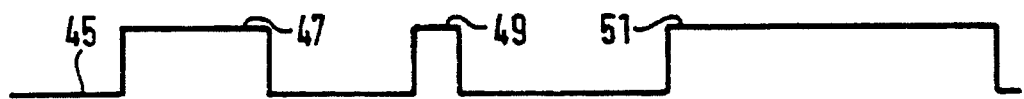
FIG. 7 illustrates the output signal from the detector of FIG. 6 according to the second embodiment.

The output signal 45 from the comparator 37 is shown in FIG. 7, with the input signal 15 as shown in FIG. 2. The P-wave generates a square wave 47 with a duration of about 40 to 100 ms.

The QRS-wave generates a square wave 49, whose duration is less than 40 ms, from the comparator 37 and the T-wave generates a square wave 51 longer than 100 ms.

The analyzer 41 in FIG. 6 determines, on the basis of the interval in which the signal from the comparator 37 falls, the type of signal, i.e., whether it represents atrial or ventricular depolarization or ventricular repolarization.

Figure 8:
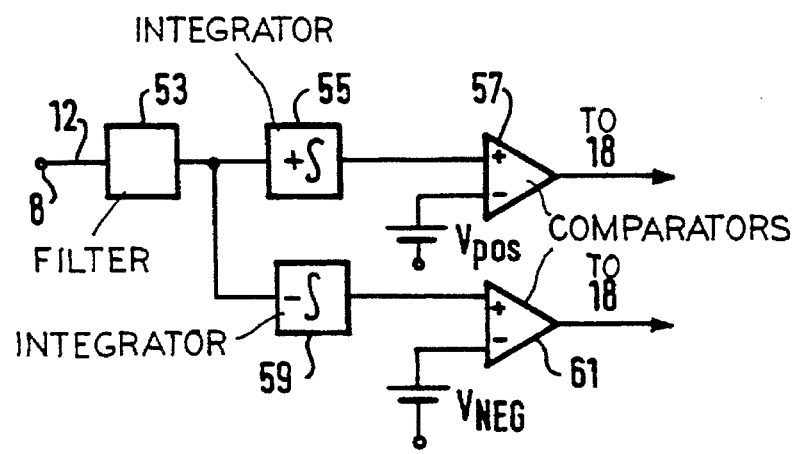
FIG. 8 shows a third embodiment of a detector which can separate monophasic from biphasic signals for use in the apparatus of the invention.

FIG. 8 shows a third embodiment of the detector 20. The signal from heart tissue is detected by the tip electrode 8 and is sent via the electrode conductor 12 to a filter 53 which, like the previous filters, can be a low-pass or a band-pass filter. The filtered signals are then sent to a first integrator 55 and a second integrator 59 respectively. The first integrator 55 only integrates signal components with a positive polarity, whereas the second integrator 59 only integrates signal components with a negative polarity. The positively integrated signal is sent to a first comparator 57, and the negatively integrated signal is sent to a second comparator 61. The respective integrated signals are compared in the respective comparators 57 and 61 with a first threshold value $V_{POS}$ and a second threshold value $V_{NEG}$ respectively. The comparators 57 and 61 then respectively generate an output signal when the integrated signals are greater or less than the threshold values $V_{POS}$, $V_{NEG}$. The output signals are sent to the control device 18 and correspond, in principle, to the output signals shown in FIG. 5. In this embodiment of the detector 20, the threshold values $V_{POS}$ and $V_{NEG}$ can be relatively small, just large enough to prevent signal noise around the baseline from being interpreted as heart signals.

A bipolar pacemaker 132 is shown in FIG. 9 connected to a heart 134 via an electrode lead 136. The electrode lead 136 has been introduced into the right ventricle and anchored with a tip electrode 138 in the upper part of the ventricular septum 140. The electrode lead 136 has been introduced into the ventricle with a gentle bend contributing to a reduction in irritation of heart tissue around the tip electrode 138. A ring electrode 142 is located at a predetermined distance from the tip electrode 138 and presses against the septum 140. The tip electrode 138 is connected to pacing electronics via a first electrode conductor 144, and the ring electrode 142 is connected to pacing electronics via a second electrode conductor 146. The pacemaker 132 also has an indifferent electrode 148 which is also connected to pacing electronics. Stimulation pulses can be delivered to ventricular tissue either unipolarly via the first electrode conductor 144, the tip electrode 138, heart tissue and the indifferent electrode 148, or bipolarly via the first electrode conductor 144, the tip electrode 138, heart tissue, the ring electrode 142 and the second electrode conductor 146. The ring electrode 142 then functions as an indifferent electrode. Both the tip electrode 138 and the ring electrode 142 can sense the electrical activity of the heart 134.

The pacemaker 132 is shown in a block diagram in FIG. 10 and has a stimulation pulse generator 150 connected to the first electrode conductor 144 and to the second electrode conductor 146. The pulse generator 150 is also connected to the indifferent electrode 148. A control device 152 controls the emission of stimulation pulses by the pulse generator 150, as well as pulse amplitude and duration. The control device 152 also controls whether the pulse generator 150 is to emit unipolar or bipolar stimulation pulses.

A detector unit 154 is connected in parallel across the output terminal of the pulse generator 150 output terminal. The detector unit 154 includes a first detector stage 156, connected across the first electrode conductor 144 and the indifferent electrode 148, to detect heart signals at the tip electrode 138, and a second detector stage 158, connected to the second electrode conductor 146 and the indifferent electrode 148, to sense heart signals at the ring electrode 142. Sensed signals are sent to the control device 152 which, in turn, can control the detector unit 154, e.g., when the detector stages 156 and 158 are to sense heart signals and the sensitivity with which the heart signals are to be sensed.

Like the unipolar pacemaker 2 in FIG. 3, the bipolar pacemaker 132 has a telemetry unit 160 through which information can be transmitted to/from the control device 152 from/to an external programming unit 162.

When atrial depolarization occurs, the atrial heart signal is sensed by the tip electrode 138 and is therefore interpreted as atrial depolarization. In the upper part of the ventricular septum 140, ventricular depolarization has a propagation direction upwardly from the bottom, i.e., it is first sensed by the ring electrode 142 and then by the tip electrode 138. The control device 152 can therefore easily distinguish between atrial depolarization, only sensed by the tip electrode 138, and ventricular depolarization, sensed both by the ring electrode 142 and the tip electrode 138.

In those instances in which the detectors 156 and 158 are not equipped with filters which eliminates the T-wave, this wave can nonetheless be identified easily. This is because ventricular repolarization has a more stochastic course of propagation than the depolarization and can therefore, e.g., be sensed simultaneously by the tip electrode 138 and the ring electrode 142, or first by the tip electrode 138 and then by the ring electrode 142. Repolarization can also be identified in the corresponding way as with the unipolar pacemaker 2.

Ventricular repolarization has a relatively constant amplitude when it follows spontaneous depolarization. Since the control device 152 also senses the amplitude of heart signals, the repolarization signal can be easily identified. This circumstance can also be utilized for distinguishing between spontaneous and stimulated ventricular depolarizations.

If ventricular repolarization is identified, identification of depolarization becomes possible, since ventricular repolarization cannot follow atrial depolarization without an intervening ventricular depolarization.

Like the unipolar pacemaker 2, the bipolar pacemaker 132 can be devised to sense whether heart signals are monophasic or biphasic and to measure the interval between various depolarizations and repolarizations. If heart signals are sensed as to whether they are monophasic or biphasic at the tip electrode 138, the bipolar pacemaker 132 can operate solely in a unipolar mode, i.e. if the second electrode conductor 146 broke, the pacemaker 138 would operate in the same way as the unipolar pacemaker 2.

A number of the described functions can be used in the corresponding manner with both unipolar and bipolar electrodes.

Although modifications and changes may be suggested by those skilled in the art, it is the intention of the inventors to embody within the patent warranted hereon all changes and modifications as reasonably and properly come within the scope of their contribution to the art.

I claim as my invention:

1. A method for determining whether electrical signals obtained from a heart having a ventricular septum are caused by an atrial depolarization of the heart or by a ventricular depolarization of the heart, comprising the steps of:

positioning an electrode surface in contact with the ventricular septum in said heart for sensing electrical signals arising in the ventricular septum;

obtaining electrical signals with said electrode surface arising in said ventricular heart tissue located nearest the atrial half of the heart; and analyzing said electrical signals to distinguish electrical signals caused by atrial depolarization from electrical signals caused by ventricular depolarization.

2. A method as claimed in claim 1 comprising the additional step of:

introducing said electrode surface into said heart with an electrode lead carrying said electrode surface, and wherein the step of positioning said electrode surface is further defined by positioning said electrode surface at an upper part of said ventricular septum with said electrode lead forming a gradual bend in the right ventricle of said heart.

3. A method as claimed in claim 1 wherein the step of analyzing said electrical signals to distinguish electrical signals caused by atrial depolarization from electrical signals caused by ventricular depolarization is further defined by the steps of:

identifying whether said electrical signals have a monophasic signal shape or a biphasic signal shape;

identifying electrical signals having a monophasic signal shape as electrical signals arising from atrial depolarizations; and identifying electrical signals having a biphasic signal shape as electrical signals arising from ventricular depolarization.

4. A method as claimed in claim 3 comprising the additional steps of:

identifying a duration of the monophasic signal shape of each electrical signal having a monophasic signal shape; and identifying only electrical signals having a duration of said monophasic signal shape which is less than a predetermined duration as electrical signals arising from atrial depolarization.

5. A method as claimed in claim 1 comprising the additional steps of:

positioning a second electrode surface in said heart for sensing additional electrical signals at or in a region surrounding said ventricular septum at a predetermined distance from said electrode surface toward the apex;

obtaining said additional electrical signals from said second electrode surface;

analyzing said electrical signals to distinguish electrical signals caused by atrial depolarization from electrical signals caused by ventricular depolarization.

6. A medical apparatus comprising:

an electrode lead carrying an electrode surface thereon, said electrode lead adapted to be positioned in the right ventricle of a heart having a ventricular septum with said electrode surface disposed in contact with an upper part of the ventricular septum;

detector means, electrically connected to said electrode surface through said electrode lead, for sensing electrical signals arising in the region of said ventricular septum, said detector means generating sensed electrical signals; and control means, supplied with said sensed electrical signals from said detector means, for distinguishing electrical signals arising due to atrial depolarization from electrical signals arising due to ventricular depolarization by analyzing said sensed electrical signals, said control means comprising a low-pass filter for eliminating high-frequency noise present in said sensed electrical signals, said low-pass filter generating a filtered signal having an amplitude, first comparator means for comparing the amplitude of said filtered signal with a first threshold value and for emitting an output signal when said amplitude of said filtered signal exceeds said first threshold value, and second comparator means for comparing said amplitude of said filtered signal with a second threshold value and for emitting an output signal when said amplitude of said filtered signal is less than said second threshold value, and said control means generating a signal indicating a sensed electrical signal as arising due to an atrial depolarization if only said first comparator means emits an output signal, and generating an output signal indicating a sensed electrical signal as arising due to ventricular depolarization if both said first and second comparator means respectively generate an output signal.

7. An apparatus as claimed in claim 6 wherein said control means further comprises timer means for measuring a time during which said first comparator means emits an output signal, said control means generating an output signal indicating a sensed electrical signal as arising from an atrial depolarization only if said first comparator means emits an output signal having a duration as measured by said timer means which is less than a predetermined duration.

8. An apparatus as claimed in claim 6 further comprising a further electrode surface carried on said electrode lead at a predetermined distance from said electrode surface and adapted for contacting the ventricular septum of said heart at said predetermined distance from said electrode surface toward the apex, said further electrode surface being electrically connected through said electrode lead to said means for detecting, and wherein said control means comprises means for identifying a sensed electrical signal as arising due to a ventricular depolarization if said sensed electrical signal is sensed by said further electrode surface before being sensed by said electrode surface.

9. An apparatus as claimed in claim 6 further comprising:
pulse generator means for generating and delivering stimulation pulses to ventricular tissue of said heart via said electrode surface, and wherein said control means comprises means for controlling said pulse generator means dependent on said sensed electrical signals and the identification of said sensed electrical signals as arising due to an atrial depolarization or a ventricular depolarization.

10. A medical apparatus comprising:
an electrode lead carrying an electrode surface thereon, said electrode lead adapted to be positioned in the right ventricle of a heart having a ventricular septum with said electrode surface disposed in contact with an upper part of the ventricular septum;
detector means, electrically connected to said electrode surface through said electrode lead, for sensing electrical signals arising in the region of said ventricular septum, said detector means generating sensed electrical signals; and
control means, supplied with said sensed electrical signals from said detector means, for distinguishing electrical signals arising due to atrial depolarization from electrical signals arising due to ventricular depolarization by analyzing said sensed electrical signals, said control means comprising integrator means for integrating a sensed electrical signal from said detector means, said integrator means generating an integrated signal having an amplitude, comparator means for comparing said integrated signal with a predetermined threshold value and for emitting a comparator output signal when said amplitude of said integrated signal exceeds said predetermined threshold value, and timer means for measuring the duration of said comparator output signal and for comparing said duration of said comparator output signal to a predetermined time value, said control means generating an output signal identifying a sensed electrical signal as arising due to a ventricular depolarization if said duration of said comparator output signal as measured by said timer means is less than said predetermined time value and generating an output signal indicating a sensed electrical signal as arising due to an atrial depolarization if said duration of said comparator output signal as measured by said timer means is greater than said predetermined time value.

11. An apparatus as claimed in claim 10 wherein said timer means further comprises means for comparing said duration of said comparator output signal with a further predetermined time value, which is greater than said predetermined time value, and wherein said control means generates said output signal identifying a sensed electrical signal as arising due to an atrial depolarization only if said comparator output signal has a duration which is greater than said predetermined time value but less than said further predetermined time value.

12. An apparatus as claimed in claim 10 further comprising a further electrode surface carried on said electrode lead at a predetermined distance from said electrode surface and adapted for contacting the ventricular septum of said heart at said predetermined distance from said electrode surface toward the apex, said further electrode surface being electrically connected through said electrode lead to said means for detecting, and wherein said control means comprises means for identifying a sensed electrical signal as arising due to a ventricular depolarization if said sensed electrical signal is sensed by said further electrode surface before being sensed by said electrode surface.

13. An apparatus as claimed in claim 10 further comprising:
pulse generator means for generating and delivering stimulation pulses to ventricular tissue of said heart via said electrode surface, and wherein said control means comprises means for controlling said pulse generator means dependent on said sensed electrical signals and the identification of said sensed electrical signals as arising due to an atrial depolarization or a ventricular depolarization.

14. A medical apparatus comprising:
an electrode lead carrying an electrode surface thereon, said electrode lead adapted to be positioned in the right ventricle of a heart having a ventricular septum with said electrode surface disposed in contact with an upper part of the ventricular septum;
detector means, electrically connected to said electrode surface through said electrode lead, for sensing electrical signals arising in the region of said ventricular septum, said detector means generating sensed electrical signals; and
control means, supplied with said sensed electrical signals from said detector means, for distinguishing electrical signals arising due to atrial depolarization from electrical signals arising due to ventricular depolarization by analyzing said sensed electrical signals, said sensed electrical signals including signal components having a positive polarity and signal components having a negative polarity, said control means comprising:
first integrator means for integrating said signal components having a positive polarity to obtain a first integrated signal,
second integrator means for integrating said signal components having a negative polarity to obtain a first integrated signal, and
means for analyzing said first and second integrated signals to determine whether a sensed integrated signal which produced said first and second integrated signals is a monophasic signal or a biphasic signal, and for identifying a monophasic signal as arising due to an atrial depolarization and a biphasic signal as arising due to a ventricular depolarization.

15. An apparatus as claimed in claim 14 further comprising a further electrode surface carried on said electrode lead at a predetermined distance from said electrode surface and adapted for contacting the ventricular septum of said heart at said predetermined distance from said electrode surface toward the apex, said further electrode surface being electrically connected through said electrode lead to said means for detecting, and wherein said control means comprises means for identifying a sensed electrical signal as arising due to a ventricular depolarization if said sensed electrical signal is sensed by said further electrode surface before being sensed by said electrode surface.

16. An apparatus as claimed in claim 14 further comprising:

pulse generator means for generating and delivering stimulation pulses to ventricular tissue of said heart via said electrode surface, and wherein said control means comprises means for controlling said pulse generator means dependent on said sensed electrical signals and the identification of said sensed electrical signals as arising due to an atrial depolarization or a ventricular depolarization.

* * * * *